US00PP36566P2

(12) United States Plant Patent
Hansen

(10) Patent No.: US PP36,566 P2
(45) Date of Patent: Mar. 25, 2025

(54) ***ACHILLEA* PLANT NAMED 'Firefly Fuchsia'**

(50) Latin Name: ***Achillea* hybrid**
Varietal Denomination: Firefly Fuchsia

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 114 days.

(21) Appl. No.: 18/445,737

(22) Filed: Jan. 8, 2024

(51) Int. Cl.
*A01H 6/14* (2018.01)
*A01H 6/06* (2018.01)

(52) U.S. Cl.
USPC ..... Plt./263.1
CPC ..... *A01H 6/06* (2018.05)

(58) Field of Classification Search
USPC ..... Plt./263.1
CPC ..... A01H 6/14; A01H 5/02
See application file for complete search history.

*Primary Examiner* — Keith O. Robinson

(57) ABSTRACT

A new and distinct Yarrow, *Achillea* plant named 'Firefly Fuchsia', with billowy habit, medium green, moderately incised to parted foliage, and large, bright lavender-pink florets that lighten to light pink on heavily-branched compound corymbs; tall, stiff, heavily branched peduncles with deep fuchsia-pink florets that mature to light pink, beginning in late June and continuing for about seven weeks and repeating if deadheaded. The new plant is useful for landscaping, as a specimen or en masse, and as a cut flower.

1 Drawing Sheet

Botanical designation: *Achillea* hybrid.
Cultivar denomination: 'Firefly Fuchsia'.

STATEMENT REGARDING PRIOR DISCLOSURES UNDER 37 CFR 1.77(b)(6)

The first offer for sale was made by Walters Gardens, Inc. on Jan. 9, 2023. Subsequently, on Dec. 1, 2023, the claimed plant was displayed as a photograph with a brief description on a website operated by Walters Gardens, Inc. Walters Gardens, Inc. obtained the plant and all information relating thereto, from the inventor. No plants of *Achillea* 'Firefly Fuchsia' have been sold, in this country or anywhere in the world nor has any disclosure of the new plant been made more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Firefly Fuchsia', by the cultivar name, 'Firefly Fuchsia', or as the new plant. The new plant was selected by the inventor as a single seedling resulting from of a proprietary, unreleased, unnamed seedling known only by the breeder code 13-4-x (not patented) by an insect pollination from an undetermined sibling of the female parent in the controlled proximity of the female parent in a research facility of a wholesale perennial grower based in Zeeland, MI, USA. The cross was performed in early summer of 2014 and the seeds from this cross were collected on Sep. 23, 2014. The single seedling that became the new plant was then isolated, given the breeder code 14-74-15, compared in subsequent years to other Yarrow, and subsequently found to be different from all cultivars known to the discoverer.

Asexual propagation at the same nursery in Zeeland, MI, USA by shoot tip cuttings and division since August of 2016 has shown 'Firefly Fuchsia' to be stable and reproduce true to type in successive generations.

SUMMARY OF THE PLANT

*Achillea* 'Firefly Fuchsia' has not been observed in all possible environmental conditions. The phenotype may vary slightly with changes in environments such as light intensity, fertility, water availability, etc. without, however any variation in genotype.

*Achillea* 'Firefly Fuchsia' is distinct from all cultivars known to the inventor in the following traits:

1. Billowy habit about 60 cm tall and 75 cm wide;
2. Medium green moderately incised to parted foliage;
3. Heavily-branched peduncles with broad clusters of inflorescences;
4. Large, deep fuchsia-pink florets that mature to light pink;
5. Sturdy stems withstand wind and rain;
6. Long flowering period beginning late June and continuing for about seven weeks;
7. Repeat flowering if deadheaded.

Plants of *Achillea* 'Firefly Fuchsia' are most similar to: 'Firefly Peach Sky' U.S. Plant Pat. No. 32,404, 'Sassy Summer Sangria' U.S. Plant Pat. No. 31,355, 'Sassy Summer Taffy' U.S. Plant Pat. No. 31,755, 'Florachrol' U.S. Plant Pat. No. 31,620, 'Saucy Seduction' U.S. Plant Pat. No. 20,782, 'Pomegranate' U.S. Plant Pat. No. 20,763, and 'Firefly Amethyst' U.S. Plant Pat. No. 32,361.

'Firefly Peach Sky' has a larger habit, both taller and broader than the new plant, and the ray florets are light peachy-orange maturing to light yellow. 'Sassy Summer Sangria' has a larger habit and the ray floret color is a dark reddish. 'Sassy Summer Taffy' has a larger habit and the ray florets begin as purplish-red inflorescences and mature to light peachy-pink. 'Florachrol' has a smaller habit with fewer inflorescences per peduncle. 'Saucy Seduction' has a more compact habit and the ray floret ligules are less vivid reddish-purple. 'Pomegranate' has a deeper reddish ray floret color, and the foliage is more dissected. 'Firefly Amethyst' is slightly smaller and more rounded in habit, and the flowers are bright lavender pink.

The parent selection has an upright narrow habit, wider foliage and the ray florets that are more reddish purple.

BRIEF DESCRIPTION OF THE DRAWINGS

The color drawings illustrate the overall characteristics of *Achillea* 'Firefly Fuchsia' as three-year-old plants in a full-sun trial garden in Zeeland, Michigan. The colors are as true as reasonably possible given the technology available. The color values may vary slightly depending on light intensity, direction, temperature, and quality.

DETAILED BOTANICAL DESCRIPTION

Figure 1:
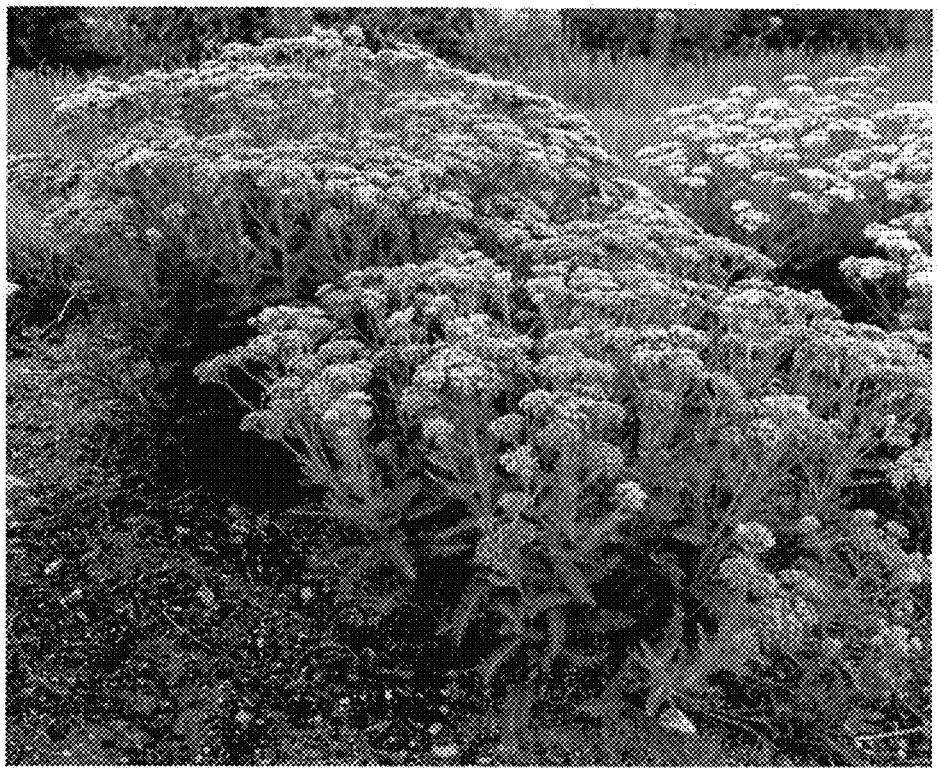
FIG. 1 shows the new plants in a trial garden.
Figure 2:
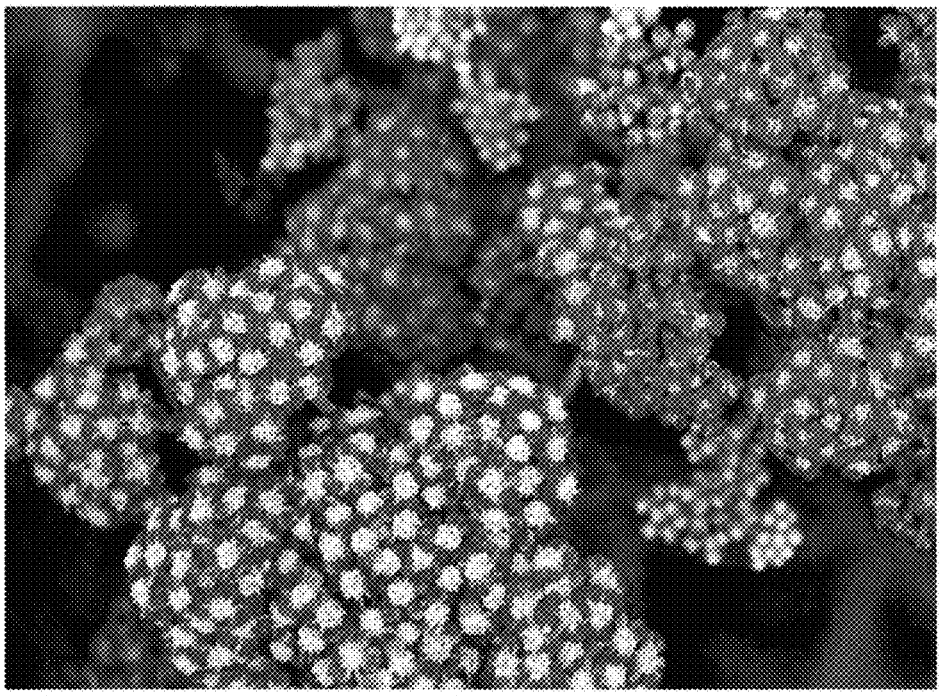
FIG. 2 shows a close-up of the inflorescences of the new plant.

The following description of the new plant is based on a three-year-old plant growing in a full-sun trial garden in Zeeland, MI, USA. Environmental conditions for the growing season daytime temperatures range between 12-30° C., and night temperatures range between 6-19° C. Color references are according to the 2015 edition of The Royal Horticultural Society Colour Chart except where ordinary dictionary terms are used.

Parentage: Female or seed parent 13-4-x; male or pollen parent was unknown insect pollination;

Asexual propagation: Shoot tip cuttings, about 10 to 14 days to initiate roots; time to finish as #1 field grown size about 9 months;

Plant habit: Dense axillary branches; upright, heavily-branched, herbaceous, winter-hardy, perennial mound; up to about 60 cm tall and 75 cm wide;

Leaves: Alternate; canescent; pinnatifid with lobules moderately incised to parted; lanceolate; acute apex; base attenuate; sessile except proximal leaves; glabrous adaxial and micro-lanulose abaxial; matte both adaxial and abaxial;

Leaf size: Up to about 13 cm long and about 4 cm wide with individual lobes to about 9 mm wide and about 18 mm long; average size about 11.5 cm long and 3 cm wide;

Leaf color: Young expanding leaves adaxial lobes nearest RHS N138C, abaxial lobes nearest RHS 138B; mature leaves adaxial lobes nearest RHS N138B, abaxial lobes nearest RHS 138B;

Foliar fragrance: Faint herbal;

Veins: Pinnate; only adaxial and abaxial midrib obvious; abaxial midrib costate, adaxial midrib flat; adaxial sparsely lanulose, abaxial lanulose;

Vein color: Adaxial midrib blend between RHS 138D and RHS 192A, abaxial midribs nearest RHS 146D;

Petiole: Channeled; lanulose; to 20 mm long and 4 mm wide at base; color nearest RHS 146C;

Stems: Upright; cylindrical; lanulose to micro-pubescent; longitudinally ridged in distal portion; to about 60 cm tall and 6 mm diameter at base;

Stem color: Between RHS 146A and RHS 137B proximally, distally between RHS 138B and RHS 138C;

Inflorescence: Radiate; composite consisting of typically five ray florets and about 27 disk florets; individual inflorescence about 7 mm diameter, about 5 mm tall from bottom of involucral bracts to top of center disk tepals; disk about 5.5 mm across; attitude mostly upright; producing branched stems with about 300 inflorescences per stem forming flat-topped, heavily-branched, compound cyme, flowering in upper 8 cm and 12 cm across; branches to about 45 cm long and 3 mm diameter at base;

Receptacle: About 3 mm tall; color nearest RHS 148C;

Inflorescence fragrance: Not detected;

Phyllaries: About 24 in two whorls; lanceolate; acute apex; truncate base; margin entire and ciliate; outer or lower set about 2.5 mm long and 1.5 mm across, inner set about 5.0 mm long and 2.0 mm across; glabrous adaxial, pubescent abaxial; tightly adpressed against ray petals;

Phyllary color: Adaxial and abaxial nearest RHS 138B and margins and midrib nearest RHS 155A;

Flowering period: Late June, for about seven weeks and repeating if deadheaded;

Inflorescence longevity: 4 to 6 days;

Inflorescence buds with ray florets still erect: Ovoid; apex truncate; base rounded; 7 mm tall and 4 mm across;

Inflorescence bud color: Ray florets while still upright exposed abaxial petal color nearest RHS NN74C; phyllaries color nearest RHS 138B and margins and midrib nearest RHS 155A;

Pedicel: Cylindrical; lanulose; strong; upright attitude; up to 6 mm long and 1 mm diameter; average about 2.5 mm long and 0.8 mm diameter;

Pedicel color: Color nearest RHS 138B;

Ray florets: Imperfect; pistillate; typically about five per inflorescence in single whorl;

Ray floret ligule: Apex rounded, emarginate with two notches about 0.5 mm deep; with an attenuate, narrow, basal claw; margin entire; opening to a 90° angle; glabrous adaxial and adaxial; about 6 mm long and about 6 mm wide; basal claw about 2 mm long and about 1 mm across;

*Young ray floret ligule color when first flat*.—Adaxial blade between RHS N74A and RHS N74B, abaxial blade nearest RHS N74B; and base nearest RHS 138D.

*Mature ray floret ligule color*.—Adaxial blade between RHS N74D and RHS 75A; abaxial nearest RHS 74D.

*Style*.—Cylindrical; about 2.5 mm long and 0.2 mm diameter; exserted; color nearest RHS 202A.

*Stigma*.—Bifid; about 0.5 mm long and 0.2 mm diameter; color initially nearest RHS NN155A maturing to nearest RHS 202D.

Disk florets: About 27 per capitulum; tubular; glabrous; consisting of five tepals, staminal tube and pistil; size about 6 mm long by 1.5 mm wide at apex;

*Tepals*.—Five; linear; fused in basal 5 mm; apex acute; margin entire; 6 mm long and 0.5 mm wide at fusion.

*Tepal color*.—Initially nearest RHS 75A adaxial and abaxial; at maturity nearest RHS 69D.

*Staminal tube*.—Made up of five adnate stamens; about 4 mm long.

*Filaments*.—Cylindrical; about 1 mm long and 0.1 mm diameter; color nearest RHS NN155A.

*Anther*.—About 1.5 mm long; color nearest RHS 17B.

*Pollen*.—Fine, round, closest to RHS 17C.

*Style*.—Bifid; cylindrical; exserted; about 4 mm long and 0.2 mm diameter; color nearest RHS NN155A.

*Stigma*.—Bifid; reflexing as it matures; about 1.5 mm long; color nearest RHS NN155A.

Seed: Flattened deltoid; acute apex and truncate base; surface glabrous; about 2.0 mm long and 0.7 mm across base;

Seed color: Between RHS 165A and RHS 165B in center and RHS 161D around edges;

*Achillea* 'Firefly Fuchsia' is tolerant of winter temperatures as low as −35° C. and summer temperatures as high as 38° C. It is not known to be tolerant of diseases and pest that are common to other *Achillea* cultivars.

I claim:

1. A new and distinct cultivar of *Achillea* plant named 'Firefly Fuchsia' as described and illustrated.

* * * * *